(12) United States Patent
Kobayashi et al.

(10) Patent No.: US 7,642,214 B2
(45) Date of Patent: Jan. 5, 2010

(54) CATALYST FOR OXIDATION OF ALKANE, PROCESS FOR PREPARING THEREOF AND PROCESS FOR PRODUCING UNSATURATED OXYGEN-CONTAINING COMPOUND

(75) Inventors: Tomoaki Kobayashi, Asa-gun (JP); Yoshimasa Seo, Tekasaki (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 251 days.

(21) Appl. No.: 11/494,846

(22) Filed: Jul. 28, 2006

(65) Prior Publication Data
US 2007/0004584 A1 Jan. 4, 2007

Related U.S. Application Data

(63) Continuation-in-part of application No. 10/450,373, filed on Jun. 10, 2003, now abandoned.

(51) Int. Cl.
*B01J 23/00* (2006.01)
*B01J 23/10* (2006.01)
*C07C 53/00* (2006.01)
*C07C 27/10* (2006.01)
*C07C 51/16* (2006.01)
*C07C 57/02* (2006.01)
*C07C 57/18* (2006.01)
*C07C 45/00* (2006.01)
*C07C 27/26* (2006.01)
*C07C 29/74* (2006.01)

(52) U.S. Cl. .................. 502/102; 502/305; 502/306; 502/309; 502/311; 502/312; 502/317; 502/321; 502/350; 502/353; 562/512.2; 562/542; 562/544; 562/545; 562/546; 562/548; 562/549; 562/598; 568/475; 568/476; 568/920

(58) Field of Classification Search ............... 502/305, 502/306, 309, 311, 312, 317, 321, 350, 353; 562/512.2, 542, 544–546, 548, 549, 598; 568/475, 476, 920
See application file for complete search history.

(56) References Cited

U.S. PATENT DOCUMENTS 4,222,899 A 9/1980 Innes et al. ............... 502/308

(Continued)

FOREIGN PATENT DOCUMENTS

EP 0 281 280 9/1988

(Continued)

OTHER PUBLICATIONS

Search Report for PCT/JP01/11180.*

(Continued)

*Primary Examiner*—Patricia L Hailey
(74) *Attorney, Agent, or Firm*—Nields, Lemack & Frame, LLC (57) ABSTRACT

An object of the present invention is to provide a highly active catalyst for producing an unsaturated oxygen-containing compound from an alkane and the catalyst comprising Mo, V, Ti and Sb or Te as the indispensable active components. The preferable catalyst is represented by formula (1) or (2) as shown below, $$Mo_{1.0}V_aTi_bX_cY_dO_e \quad (1)$$

$$Mo_{1.0}V_aTi_bX_cY_dZ_fO_e \quad (2)$$

wherein X represents Sb or Te; Y represents Nb, W or Zr; Z represents Li, Na, K, Rb, Cs, Mg, Ca or Sr; a, b, c, d, e and f represent atomic ratios of their respective elements, with $0<a<0.7$, $0<b<0.3$, $0<c<0.7$, $0\leq d<0.3$, $0<f<0.1$; e is a number determined by oxidation states of the other elements than oxygen.

6 Claims, 2 Drawing Sheets

U.S. PATENT DOCUMENTS

| | | | |
|---|---|---|---|
| 4,278,614 A | 7/1981 | Umemura et al. | 558/322 |
| 4,408,067 A | 10/1983 | Nakamura et al. | 560/215 |
| 4,892,856 A | 1/1990 | Kawajiri et al. | 502/247 |
| 5,380,933 A * | 1/1995 | Ushikubo et al. | 562/549 |
| 5,994,580 A | 11/1999 | Takahashi et al. | 562/549 |
| 6,294,685 B1 | 9/2001 | Ushikubo et al. | 558/319 |
| 6,320,075 B1 | 11/2001 | Ruedinger et al. | 562/549 |
| 6,514,902 B1 | 2/2003 | Inoue et al. | 502/305 |
| 6,563,000 B1 | 5/2003 | Yunoki et al. | 562/532 |
| 6,656,873 B2 * | 12/2003 | Chaturvedi et al. | 502/312 |
| 6,746,983 B2 | 6/2004 | Gaffney et al. | 502/312 |
| 2001/0049336 A1 | 12/2001 | Lin et al. | 502/305 |
| 2002/0072628 A1 | 6/2002 | Tu et al. | 562/545 |
| 2002/0115879 A1 | 8/2002 | Hinago et al. | 558/323 |
| 2002/0188150 A1 | 12/2002 | Gaffney et al. | 558/323 |
| 2003/0088118 A1 | 5/2003 | Komada et al. | 558/332 |
| 2004/0097368 A1 | 5/2004 | Borgmeier et al. | 502/312 |

FOREIGN PATENT DOCUMENTS

| | | |
|---|---|---|
| EP | 0 608 838 | 9/1994 |
| EP | 0 711 745 | 5/1996 |
| EP | 0 945 432 | 9/1999 |
| EP | 0 962 253 | 12/1999 |
| EP | 1 055 662 | 11/2000 |
| JP | 8-206504 | 8/1996 |
| JP | 10-17523 | 1/1998 |
| JP | 10-195036 | 7/1998 |
| JP | 2002-88012 | 3/2002 |
| JP | 2002-88013 | 3/2002 |
| JP | 2002-361085 * | 12/2002 |
| WO | 99/03825 | 1/1999 |
| WO | 00/12209 | 3/2000 |

OTHER PUBLICATIONS

Chem. Commun., 1999, 517-518; Wataru Ueda et al.; "Hydrothermal synthesis of Mo-V-M-O complex metal oxide catalysts active for partial oxidation of ethane".

The International Search Report dated Apr. 9, 2002.

The European Communication dated May 30, 2005.

* cited by examiner

CATALYST FOR OXIDATION OF ALKANE, PROCESS FOR PREPARING THEREOF AND PROCESS FOR PRODUCING UNSATURATED OXYGEN-CONTAINING COMPOUND

This application is a continuation-in-part of U.S. Ser. No. 10/450,373 filed Jun. 10, 2003 now abandoned.

TECHNICAL FIELD

The present invention relates to a catalyst for producing an unsaturated oxygen-containing compound from an alkane, particularly to a catalyst suitable for producing acrolein or acrylic acid and methacrolein or methacrylic acid by the vapor-phase catalytic oxidation of propane and isobutane respectively.

BACKGROUND ART

An unsaturated oxygen-containing compound, including an unsaturated aldehyde such as acrolein and methacrolein or an unsaturated carboxylic acid such as acrylic acid and methacrylic acid, is generally produced by the vapor-phase catalytic oxidation of propylene or isobutylene as the starting material in the presence of an oxidation catalyst. Recently however, it has come to be paid attention to the method efficient for producing an unsaturated oxygen-containing compound by using an alkane such as propane or isobutane as the starting material which is cheaper than propylene or isobutylene, and there have been proposed various catalysts to use for the said process. A MoVTe type catalyst has been disclosed by JP Laid-Open No. 279351/1994, JP Laid-Open No. 36311/1998, and JP Laid-Open No. 143244/2000. A MoVSb type catalyst has been disclosed by JP Laid-Open No. 316023/1997, JP Laid-Open No. 045664/1998, JP Laid-Open No. 118491/1998, JP Laid-Open No. 120617/1998, JP Laid-Open No. 137585/1998, JP Laid-Open No. 285637/1999, and JP Laid-Open No. 51693/2000.

The MoVTe type catalyst can give acrylic acid as the final product at a high yield, but is likely to lose the catalytic activity if used at a high temperature. Because the tellurium which is one of the essential components of the said catalyst is easy to be evaporated.

In the manufacturing process of the MoVSb type catalyst, molecular oxygen or hydrogen peroxide is added to increase the acrylic acid yield. However, the disclosed reaction temperature is as high as 380° C. or above, there is a problem that the catalyst does not have a sufficient catalytic activity. Therefore, further improvement in the catalytic activity is needed in view of running cost and catalyst life span.

The various catalysts have been proposed to obtain an unsaturated oxygen-containing compound at a high yield from an alkane. But none of them has reached to a commercially applicable level yet.

The commercially applicable catalyst must attain an appropriate alkane conversion, a good acrylic acid selectivity and finally a sufficient acrylic acid yield. Further, its long term stable performance is needed to be kept.

DISCLOSURE OF THE INVENTION

The present inventors have studied to find out a catalyst for producing an unsaturated oxygen-containing compound such as α,β-unsaturated aldehyde or/and unsaturated carboxylic acid, concretely (meth)acrolein or/and (meth)acrylic acid from an alkane such as a C3-C8 alkane, concretely a C3 or C4 alkane, that is, propane or isobutane. As a result, it has been found out that the objective unsaturated oxygen-containing compound can be produced at a lower temperature in the presence of a catalyst comprising a complex oxide containing molybdenum, vanadium, titanium and specific metal(s). The present invention is completed based on this finding. Namely the present invention is as follows:

(1) A catalyst for producing an unsaturated oxygen-containing compound from an alkane, comprising Mo, V, Ti and Sb or Te as the indispensable active component elements.

(2) A catalyst according to the above item (1), further comprising at least one element selected from the group consisting of Li, Na, K, Rb, Cs, Mg, Ca and Sr as the active component element.

(3) A catalyst according to the above item (1), wherein said catalyst is represented by general Formula (1) as shown below, $$Mo_{1.0}V_aTi_bX_cY_dO_e \quad (1)$$

wherein, X represents at least one element selected from the group consisting of Sb and Te; Y represents at least one element selected from the group consisting of Nb, W and Zr; a, b, c, d and e represent atomic ratios of their respective elements, with $0<a<0.7$, $0<b<0.3$, $0<c<0.7$, $0\leq d<0.3$; e is a number determined by the oxidation states of the other elements than oxygen.

(4) A catalyst according to the above item (2), wherein said catalyst is represented by general Formula (2) as shown below, $$Mo_{1.0}V_aTi_bX_cY_dZ_fO_e \quad (2)$$

wherein X, Y, a, b, c, d and e show the same meanings as in the formula (1). Z represents at least one element selected from the group consisting of Li, Na, K, Rb, Cs, Mg, Ca and Sr and f is an atomic ratio of Z, with $0<f<0.1$.

(5) A method for preparing the catalyst described in the above item (1) or (2), comprising a process for mixing starting material compounds containing elements (active component elements) of said catalyst with water to prepare a slurry solution and a process for heating and pressuring said slurry solution.

(6) A method according to the above item (5), comprising calcining the product obtained by said heating and pressuring, wherein said calcining comprises the first calcining process carried out in the presence of oxygen gas and the second calcining process carried out in the presence of inert gas.

(7) A method according to the above item (6), wherein a temperature difference between said first calcining process and said second calcining process is 150-400° C.

(8) A method according to the above item (5), wherein said first calcining process is carried out at 250-350° C. and said second calcining process is carried out at 500-650° C.

(9) A catalyst according to the above item (1) or (2), wherein said catalyst is used for producing acrolein and/or acrylic acid from propane.

(10) A complex oxide catalyst comprising Mo, V, Ti and Sb or Te as the indispensable active component elements, having a needle crystal form.

(11) A method for producing an unsaturated oxygen-containing compound by the vapor-phase catalytic oxidation of an alkane, characterized by using a catalyst according to any one of the above items (1)-(3).

BEST MODE FOR CARRYING OUT THE INVENTION

The present invention will be described in detail below.

The catalyst of the present invention comprises a complex oxide containing Mo, V, Ti and Sb or Te (hereinafter called as the A element group) as the indispensable active component elements and the complex oxide may contain the other active component elements. Other active component elements are not limited to any particular ones. The complex oxide generally contains any one of Sb and Te, but may contain the both. When containing Sb, the specific surface area of the catalyst is likely to increase in comparison with the one which does not contain Sb. The said increase in the specific surface area contributes to the high catalytic activity (high conversion). When containing Te as a component element of the catalyst, on the other hand, the specific surface area of the catalyst does not increase very much. The obtained catalyst, in comparison with the one which contains Sb, has a higher catalytic activity at a little higher reaction temperature. A target compound such as acrylic acid can be obtained with high conversion and good selectivity. As mentioned above, however, it needs to be carefully watched not to lose the catalytic activity because Te is likely to be evaporated.

One of the preferable examples of the present invention is a catalyst containing, in addition to the elements of the A element group, at least one element selected from the group (hereinafter called as the B element group) consisting of Li, Na, K, Rb, Cs, Mg, Ca and Sr. Among these elements of the B element group, K and Rb are preferable, and K is more preferable. The catalyst containing any element(s) of the B element group has a higher acrylic acid selectivity than the catalyst containing the elements of the A element group only.

The method for manufacturing the catalyst of the present invention is not limited to any particular one. The catalyst can be produced, for example, by a method that the starting material compounds, containing the catalyst composing element which can be either singular or plural (hereinafter called the starting material compounds), are mixed with water to prepare a slurry solution and then the slurry solution is dried and calcined if necessary. The calcining temperature is generally 300-900° C., and the calcining time is generally 1-30 hours. The more preferable method for manufacturing the catalyst of the present invention is to prepare the slurry solution as mentioned above, successively the slurry solution is heated, pressured and then dried.

The starting material compound to use for manufacturing the catalyst of the present invention is not limited to any particular one, provided it can be calcined under air to decompose into an oxide.

The starting material compound for an element of the A element group includes a molybdenum-containing compound such as ammonium molybdate, molybdenum trioxide, molybdic acid and sodium molybdate; a vanadium-containing compound such as vanadium oxide, ammonium vanadate, vanadyl oxosulfate; a titanium-containing compound such as titanium oxide, titanium ammonium oxalate and titanium sulfate; an antimony-containing compound such as antimony trioxide, antimony sulfate and antimony acetate; and a tellurium-containing compound such as tellurium dioxide and telluric acid.

The starting material compound for an element of the B element group includes the oxide, the chloride, the sulfate, the nitrate, the acetate, carbonate or the hydroxide of the element of the B element group. It includes concretely lithium oxide, lithium chloride, lithium nitrate, lithium carbonate, lithium hydroxide, sodium oxide, sodium chloride, sodium nitrate, sodium carbonate, sodium hydrogen carbonate, sodium hydroxide, potassium oxide, potassium chloride, potassium nitrate, potassium carbonate, potassium hydrogen carbonate, potassium acetate, potassium hydroxide, rubidium carbonate, rubidium nitrate, rubidium oxide, rubidium hydroxide, cesium carbonate, cesium nitrate, cesium acetate, cesium oxide, cesium hydroxide, calcium carbonate, calcium hydrogen carbonate, calcium nitrate, calcium acetate, calcium oxide, calcium hydroxide, strontium carbonate, strontium nitrate, strontium acetate, strontium oxide and strontium hydroxide.

The catalyst of the present invention may contain other active component element(s) than the elements of the A element group and the B element group. At least one element selected from the group (hereinafter called the C element group) consisting of Nb, W and Zr is preferable for the other active component element. The starting material compound for this optional element includes the oxide, the chloride, the sulfate and the nitrate of the optional component element. It includes concretely niobic acid, niobium oxide and niobium hydrogen oxalate for a starting material compound of niobium; ammonium paratungstate, tungstic acid and tungsten oxide for a starting material compound of tungsten; and zirconium oxide, zirconium nitrate and zirconium acetate for a starting material compound of zirconium. If any ammonium salt is used for a starting material compound, an appropriate preparation condition is preferable to determine so that the catalyst may contain no remaining ammonium group.

The complex oxide composing a catalyst of the present invention may have any optional constituent provided it contains the elements of the A element group. The complex oxide, if it contains a combination of the elements of the A element group with any elements of the C element group, has preferably a composition represented by formula (1) as shown below, $$Mo_{1.0}V_aTi_bX_cY_dO_e \qquad (1)$$

wherein X represents at least one element selected from the group consisting of Sb and Te; Y represents at least one element selected from the group consisting of Nb, W and Zr; a, b, c, d and e represent atomic ratios of their respective elements, with $0<a<0.7$, $0<b<0.3$, preferably $0.005<b<0.1$, $0<c<0.7$, $0\leq d<0.3$, preferably $0\leq d<0.1$; e is a number determined by the oxidation states of other elements than oxygen.

The complex oxide, if it contains further any elements of the B element group, has preferably a composition represented by formula (2) as shown below, $$Mo_{1.0}V_aTi_bX_cY_dZ_fO_e \qquad (2)$$

wherein X, Y, a, b, c, d and e show the same meanings as in the formula (1). Z represents at least one element selected from the group consisting of Li, Na, K, Rb, Cs, Mg, Ca and Sr; f is an atomic ratio of Z, with $0<f<0.1$, preferably $0.005<f<0.1$.

As described above, the catalyst of the present invention can be prepared by mixing the compounds containing active component element(s) with water to prepare a slurry solution followed by drying. But the catalyst is preferably prepared by a hydrothermal synthesis method including a process for heating and pressuring the slurry solution before drying.

The powder obtained by the hydrothermal synthesis method is observed by an electron microscope to have an appearance of needle crystal. Such a crystal is generally not observed by an electron microscope when the hydrothermal synthesis method is not carried out. Therefore, it can be thought the needle crystal was brought about by the hydrothermal synthesis method.

According to the hydrothermal synthesis method, starting material compounds are generally dissolved or dispersed in water in temperature between the normal temperature and 100° C. to prepare a slurry solution, which is then treated in an autoclave. The amount of water to use, though it is not particularly limited provided it is sufficient to prepare a slurry solution, is generally 0.5-20 part by mass, preferably 1-10 part by mass, more preferably 1-6 part by mass relative to 1 part by mass of the starting material compounds.

The hydrothermal synthesis is not limited to any particular one provided it is a treatment for general hydrothermal reaction. The above slurry solution may be heated at a high temperature of more than 100° C. in an autoclave to treat for the hydrothermal reaction. The reaction may be carried out in air, but it is preferable that the air existing in the autoclave is replaced partly or wholly with an inert gas such as nitrogen gas and helium gas before starting the reaction. The reaction temperature for the hydrothermal synthesis is generally 110° C. or more, preferably 130° C. or more, more preferably 140° C. or more, and generally 400° C. or less, preferably 300° C. or less, more preferably 250° C. or less. The reaction time is generally 1-100 hours.

The pressure within the autoclave is usually a saturated vapor pressure, but optionally may be higher than the saturated vapor pressure, and the slurry solution may be stirred throughout the hydrothermal synthesis.

After the hydrothermal reaction terminates, the reaction solution is cooled to form a solid product, which is then separated and dried. The method for separating the product is not limited to any particular one provided it can separate solid from liquid, and is preferably to filtrate, wash and dry.

The product thus obtained may be used for a catalyst of the present invention as it is, but is preferably treated with the calcining to complete a catalyst of the present invention. The calcining treatment may be carried out by one step at 300-900° C., for 1-30 hours in air, but is preferably carried out by two steps in their respective different atmospheres as described below.

The temperature difference between the first calcining treatment and the second calcining treatment is preferably 150° C. or more, more preferably 200° C. or more and is preferably 500° C. or less, more preferably 400° C. or less. The first calcining treatment is carried out at 200° C. or more and 400° C. or less, preferably at 250-350° C. for 0.5-12 hours in the presence of oxygen gas (for example, in air). The second calcining treatment is carried out at 400° C. or more and 700° C. or less, preferably at 500-650° C. for 0.5-10 hours in an inert gas such as nitrogen and helium.

There are some cases that the two calcining treatments lower the catalytic performance if carried out outside the above ranges of calcining temperature and time. It is undesirable especially because it lowers an unsaturated oxygen-containing compound selectivity.

The complex metal oxide obtained after calcining treatment may be used for a catalyst of the present invention as it is, but is preferably pulverized to use depending on the cases.

The catalyst of the present invention thus obtained is a needle crystal having a specific surface area of 1-50 $m^2/g$, preferably 2-50 $m^2/g$, more preferably 2-20 $m^2/g$.

The catalyst of the present invention is presumed to increase the catalytic activity by containing Ti together with Mo, V and Sb or Te as a component element. Further, when the methods of the hydrothermal synthesis and the two steps calcinations are applied in a manufacturing process of a catalyst of the present invention, the preferable effect was brought about in the catalytic activity compared with the cases in which the above mentioned methods have not been applied. It is thus presumed that the combination of those two methods and the above mentioned component elements brings about the effective result in the activity of the catalyst.

A catalyst of the present invention that contains at least one element selected from the B group also can be obtained by the following method. The compounds containing the catalyst composing elements, excluding the elements of the B element group, are subjected to the hydrothermal synthesis and the calcination as described above to get a calcinated powder. The powder is dispersed in a solution containing the elements of the B element group (an aqueous solution or an aqueous dispersion of compounds containing the elements of the B element group), filtered, washed and dried to get the catalyst of the present invention. The catalyst obtained after drying may be further calcined.

The catalyst thus obtained can be suitably used for producing an unsaturated oxygen-containing compound such as acrolein, acrylic acid or methacrolein, methacrylic acid by the vapor-phase catalytic oxidation of an alkane (preferably a C3-C8 alkane, more preferably a C3-C4 alkane) such as propane or isobutane. The catalyst can be most suitably used for producing acrolein or acrylic acid from propane. In the present invention, an unsaturated oxygen-containing compound means a carbonyl group-containing compound, preferably a compound having both an ethylenic unsaturated bond and a carbonyl group. When producing (meth)acrolein and/or (meth)acrylic acid as the target compound, gases other than the target compound produced in the process are propylene and acetic acid. The propylene is possibly formed with a selectivity of about 10-30%. The target acrolein or acrylic acid, for example, can be obtained from the propylene in the succeeding process by using a catalyst for the vapor-phase catalytic oxidation of propylene.

The composition ratio (mole ratio) of the raw material gases for the vapor-phase catalytic oxidation reaction is not limited to any particular one. However, alkane:oxygen:water vapor:dilution gas is generally 1:0.1-10:0-70:0-20, preferably 1:0.5-3.0:3.0-20:0-10. The preferable dilution gas includes nitrogen and carbon dioxide gas.

The vapor-phase catalytic oxidation reaction may be carried out either under a pressure or a reduced pressure, but is preferably proceeded under an atmospheric pressure. The reaction temperature is generally 250-450° C., preferably 280-420° C., and more preferably 300-380° C.

The space velocity (SV) for supplying the raw material gas is generally 100-100,000 $hr^{-1}$, preferably 400-30,000 $hr^{-1}$.

The catalyst of the present invention is applicable for any reaction style of fixed bed, fluid bed and moving bed.

For a fixed bed reaction vessel, a coated catalyst obtained by coating the catalyst powder on a spherical carrier made of silica, alumina, silicone carbide and the like, or a molded catalyst obtained by tableting the catalyst powder is profitably used. For a fluid bed or moving bed reaction vessel, the particle catalyst of a complex metal oxide prepared by further adding a reaction-inactive material such as silica to increase abrasion resistance is profitably used, wherein the particle catalyst has a size of about tens micron uniformly. The catalyst of the present invention can restrain an alkane conversion to keep a high selectivity to the target unsaturated oxygen-containing compound in the reaction, and can also be used in a reaction system for recycling an unreacted alkane in the reaction vessel after separating the reaction product.

EXAMPLE

The present invention will be described below in detail by the examples, but is not limited to the examples unless beyond the gist of the present invention.

In the examples, propane conversion and acrylic acid selectivity have their respective definitions as follows:

Propane conversion(mol%) = (moles of propane supplied − moles of unreacted propane)×

100 Acrylic acid selectivity(mol%)

= (moles of acrylic acid produced)/

(moles of propane supplied − moles of unreacted propane)×

100

The catalyst composition was calculated based on a ratio of added starting material compounds (excepting K as measured by the emission spectroanalysis).

Example A1

Preparation of Catalyst

Ammonium molybdate (6.00 g) was dissolved in 30 ml of distilled water. Antimony sulfate (0.85 g) was added to the solution at 80° C. under stirring, followed by adding 2.53 g of vanadyl oxosulfate and 0.22 g of titanium ammonium oxalate further. After sufficient stirring, the solution was put in an autoclave (volume capacity 60 ml) and hydrothermal synthesis was carried out at 175° C. for 24 hours. The product thus obtained was filtered to separate, washed, dried at 40° C. for a day, calcined at 280° C. for 1 hour under air stream and calcined successively at 600° C. for 2 hours under nitrogen stream to get a catalyst of the present invention having a composition (excluding oxygen, hereinafter likewise) of $Mo_{1.0}V_{0.3}Ti_{0.025}Sb_{0.1}$.

Estimate Test of the Catalysts

A fixed bed flow type reaction vessel was used. The catalyst (1.2 ml) was pulverized sufficiently, diluted with 3.6 ml of silicone carbide powder and packed in a Pyrex tube having an inner diameter of 12 mm. A raw material mixture gas composed of propane, oxygen, water vapor and nitrogen was flowed through the tube at a flow rate of propane/oxygen/water vapor/nitrogen=3/4.5/21/18 (ml/min) to react at 320° C. The reaction product was analyzed by gas chromatography.

Specific Surface Area Measurement

The flow Sorp II 2300 made by Micro Meritics was used to measure. About 0.3 g of the catalyst was previously treated at 200° C. in an inert gas. A nitrogen/helium mixture gas was flowed to measure the specific surface area on the base of nitrogen absorption.

The results of the estimate test of the catalyst and specific surface area measurement are shown in Table 1.

Example A2

The catalyst of the present invention having a composition of $Mo_{1.0}V_{0.3}Ti_{0.025}Sb_{0.1}$ was obtained by the same way as described in the Example A1, except that 0.21 g of titanium (II)sulfate was used in place of 0.22 g of titanium ammonium oxalate.

With respect to the catalyst obtained, the estimation test and specific surface area measurement were carried out in the same way as in Example A1. The results are shown in Table 1.

Example A3

The catalyst of the present invention having a composition of $Mo_{1.0}V_{0.3}Ti_{0.025}Sb_{0.1}$ was obtained by the same way as described in Example A1, except that 0.28 g of titanium(II) sulfate was used in place of 0.22 g of titanium ammonium oxalate.

With respect to the catalyst obtained, the estimation test and specific surface area measurement were carried out in the same way as in Example A1. The results are shown in Table 1.

Comparative Example 1

The catalyst having a composition of $Mo_{1.0}V_{0.3}Sb_{0.1}$ for comparison was obtained by the same way as described in the Example A1, except no titanium ammonium oxalate was added.

With respect to the catalyst obtained, the estimation test and specific surface area measurement were carried out in the same way as in Example A1. The results are shown in Table 1.

Example A4

The catalyst of the present invention having a composition of $Mo_{1.0}V_{0.3}Ti_{0.025}Sb_{0.1}Nb_{0.025}$ was obtained by the same way as described in the Example A1, except 0.15 g of niobic acid was added after addition of the titanium ammonium oxalate in Example A1.

With respect to the catalyst obtained, the estimation test and specific surface area measurement were carried out in the same way as in Example A1. The results are shown in Table 1.

Example A5

The catalyst of the present invention having a composition of $Mo_{1.0}V_{0.3}Ti_{0.025}Sb_{0.1}W_{0.025}$ was obtained by the same way as described in the Example A4, except 0.21 g of tungstic acid was used in place of 0.15 g of niobic acid in Example A4.

With respect to the catalyst obtained, the estimation test and specific surface area measurement were carried out in the same way as in Example A1. The results are shown in Table 1.

Example A6

The catalyst of the present invention having a composition of $Mo_{1.0}V_{0.3}Ti_{0.025}Sb_{0.1}Zr_{0.025}$ was obtained by the same way as described in the Example A1, except 0.29 g of zirconium sulfate was used in place of 0.15 g of niobic acid in Example A4.

With respect to the catalyst obtained, the estimation test and specific surface area measurement were carried out in the same way as in Example A1. The results are shown in Table 1.

TABLE 1

| Example | Reaction Temperature (° C.) | Propane Conversion (%) | Acrylic Acid Selectivity (%) | Catalyst S.S.A. (m$^2$/g) |
|---|---|---|---|---|
| A1 | 320 | 36 | 34 | 18 |
| A2 | 320 | 29 | 34 | 19 |
| A3 | 320 | 27 | 35 | 16 |
| Comparative Ex1 | 320 | 11 | 28 | 6 |
| A4 | 320 | 47 | 25 | 17 |
| A5 | 320 | 33 | 31 | 18 |
| A6 | 320 | 29 | 29 | 13 |

(note)
S.S.A.: Specific Surface Area

Example A7

Ammonium molybdate (6.00 g) was dissolved in 30 ml of distilled water. Tellurium dioxide (0.85 g) was added to the solution at room temperature under stirring, followed by adding 4.21 g of vanadyl oxosulfate, 1.65 g of niobium hydrogen oxalate and 0.22 g of titanium ammonium oxalate further. After sufficient stirring, the solution was put in an autoclave (volume capacity 60 ml) and hydrothermal synthesis was carried out at 175° C. for 24 hours. The product thus obtained was filtered to separate, washed, dried at 40° C. for a day, calcined at 300° C. for 2 hours under air stream and calcined successively at 600° C. for 2 hours under nitrogen stream to get a catalyst of the present invention having a composition of $Mo_{1.0}V_{0.5}Ti_{0.025}Te_{0.17}Nb_{0.058}$.

With respect to the catalyst obtained, the specific surface area measurement was carried out in the same way as in Example A1. The obtained specific surface area was 3 m$^2$/g.

Further, the estimation test of catalyst obtained was carried out in the same way as in Example A1 except the reaction temperature was changed to 380° C. The propane conversion was 42% and acrylic acid selectivity was 60%.

Example B1

Preparation of Catalyst

Ammonium molybdate (6.00 g) was dissolved in 30 ml of distilled water. Antimony sulfate (0.85 g) was added to the solution at 80° C. under stirring, followed by adding 2.53 g of vanadyl oxosulfate, 0.22 g of titanium ammonium oxalate and 0.08 g of potassium nitrate further. After sufficient stirring, the solution was put in an autoclave (volume capacity 60 ml) and hydrothermal synthesis was carried out at 175° C. for 24 hours. The product thus obtained was filtered to separate, washed, dried at 40° C. for a day, calcined at 280° C. for 1 hour under air stream and calcined successively at 600° C. for 2 hours under nitrogen stream to get a catalyst of the present invention having a composition of $Mo_{1.0}V_{0.3}Ti_{0.025}Sb_{0.1}K_{0.016}$.

Estimate Test of the Catalyst

The reaction tests were carried out in the same way as in Example A1, except that the reaction temperature was changed to 360° C. The results are shown in Table 2.

Example B2

The catalyst of the present invention having a composition of $Mo_{1.0}V_{0.3}Ti_{0.025}Sb_{0.1}Rb_{0.015}$ was obtained by the same way as described in the Example B1, except that 0.12 g of rubidium nitrate was used in place of 0.08 g of potassium nitrate.

The estimation test of catalyst obtained was carried out in the same way as in Example B1. The results are shown in Table 2.

Example B3

The catalyst of the present invention having a composition of $Mo_{1.0}V_{0.3}Ti_{0.025}Sb_{0.1}Cs_{0.015}$ was obtained by the same way as described in the Example B1, except that 0.16 g of cesium nitrate was used in place of 0.08 g of potassium nitrate.

The estimation test of catalyst obtained was carried out in the same way as in Example B1. The results are shown in Table 2.

Example B4

The catalyst of the present invention having a composition of $Mo_{1.0}V_{0.3}Ti_{0.025}Sb_{0.1}K_{0.010}$ was obtained by the same way as described in the Example B1, except the amount of potassium nitrate was changed from 0.08 g to 0.03 g.

The estimation test of catalyst obtained was carried out in the same way as in Example B1. The results are shown in Table 2.

Example B5

The catalyst of the present invention having a composition of $Mo_{1.0}V_{0.3}Ti_{0.025}Sb_{0.1}K_{0.027}$ was obtained by the same way as described in the Example B1, except the amount of potassium nitrate was changed from 0.08 g to 0.16 g.

The estimation test of catalyst obtained was carried out in the same way as in Example B1. The results are shown in Table 2.

Example B6

The catalyst of the present invention having a composition of $Mo_{1.0}V_{0.3}Ti_{0.025}Sb_{0.1}K_{0.050}$ was obtained by the same way as described in the Example B1, except the amount of potassium nitrate was changed from 0.08 g to 0.24 g.

The estimation test of catalyst obtained was carried out in the same way as in Example B1. The results are shown in Table 2.

Example B7

Ammonium molybdate (6.00 g) was dissolved in 30 ml of distilled water. Antimony sulfate (0.85 g) was added to the solution at 80° C. under stirring, followed by adding 2.53 g of vanadyl oxosulfate, 0.22 g of titanium ammonium oxalate, 0.15 g of niobic acid and 0.16 g of potassium nitrate further. After sufficient stirring, the solution was put in an autoclave (volume capacity 60 ml) and hydrothermal synthesis was carried out at 175° C. for 24 hours. The product thus obtained was filtered to separate, washed, dried at 40° C. for a day, calcined at 280° C. for 1 hour under air and calcined successively at 600° C. for 2 hours under nitrogen gas to get a catalyst of the present invention having a composition of $Mo_{1.0}V_{0.3}Ti_{0.025}Sb_{0.1}Nb_{0.025}K_{0.046}$.

The estimation test of the catalyst obtained was carried out in the same way as in Example B1. The results are shown in Table 2.

Example B8

The catalyst of the present invention having a composition of $Mo_{1.0}V_{0.3}Ti_{0.025}Sb_{0.1}W_{0.025}K_{0.030}$ was obtained by the same way as described in the Example B7, except 0.21 g of tungstic acid was used in place of 0.15 g of niobic acid in Example B7.

The estimation test of catalyst obtained was carried out in the same way as in Example B1. The results are shown in Table 2.

Example B9

The catalyst of the present invention having a composition of $Mo_{1.0}V_{0.3}Ti_{0.025}Sb_{0.1}Zr_{0.025}K_{0.029}$ was obtained by the same way as described in the Example B7, except 0.29 g of zirconium sulfate was used in place of 0.15 g of niobic acid in Example B7.

The estimation test of catalyst obtained was carried out in the same way as in Example B1. The results are shown in Table 2.

Example B10

Preparation of Catalyst

Ammonium molybdate (6.00 g) was dissolved in 30 ml of distilled water. Antimony sulfate (0.85 g) was added to the solution at 80° C. under stirring, followed by adding 2.53 g of vanadyl oxosulfate and 0.22 g of titanium ammonium oxalate further. After sufficient stirring, the solution was put in an autoclave (volume capacity 60 ml) and hydrothermal synthesis was carried out at 175° C. for 24 hours. The product thus obtained was filtered to separate, washed, dried at 40° C. for a day, calcined at 280° C. for 1 hour under air stream and calcined successively at 600° C. for 2 hours under nitrogen stream to get a complex metal oxide.

The complex metal oxide obtained was dispersed in 100 ml of the aqueous solution containing 1.18 g of potassium nitrate. This mixture was filtered to separate, washed and dried at 40° C. for 1 day to obtain a catalyst of the present invention having a composition of $Mo_{1.0}V_{0.3}Ti_{0.025}Sb_{0.1}K_{0.024}$.

The estimation test of catalyst obtained was carried out in the same way as in Example B1. The results are shown in Table 2.

TABLE 2

| Example | Reaction Temperature (° C.) | Propane Conversion (%) | Acrylic Acid Selectivity (%) |
|---|---|---|---|
| B1 | 360 | 36 | 48 |
| B2 | 360 | 27 | 49 |
| B3 | 360 | 14 | 37 |
| B4 | 360 | 37 | 39 |
| B5 | 360 | 30 | 59 |
| B6 | 360 | 22 | 56 |
| B7 | 360 | 38 | 51 |
| B8 | 360 | 12 | 49 |
| B9 | 360 | 24 | 49 |
| B10 | 360 | 39 | 49 |

Example C

The following experiments were conducted to compare the form of the catalyst obtained by treating aqueous raw material mixtures, which were prepared by dissolving the compounds for catalyst components, according to the method shown in Example B1 with the forms of catalysts obtained by drying aqueous raw material mixtures prepared the same as mentioned above and calcining the obtained dry raw material mixtures according to the method shown in U.S. Patent Publication No. 2002/0115879 (Hinago et al.) and WO 99/03825, respectively, and further to compare the performance of the present catalyst obtained by the treatment mentioned above with the performance of the catalyst obtained by drying and calcining according to the method shown in WO 99/03825.

(I) Experiment:

(A) Preparation of Catalysts (1) The Preparation of an Aqueous Raw Material Mixture:

Ammonium molybdate (12 g) was dissolved in 30 ml of distilled water. Antimony sulfate (1.7 g) was added to the solution at 80° C. under stirring, followed by adding 5.06 g of vanadyl oxosulfate, 0.44 g of titanium ammonium oxalate and 0.16 g of potassium nitrate further. Then, the mixture was sufficiently stirred to obtain an aqueous raw material mixture (solution).

(2) The Preparation of Present Catalyst:

The aqueous raw material mixture obtained by the above (1) was put in an autoclave (volume capacity 100 ml) and hydrothermal synthesis was carried out at 175° C. for 24 hours. The product thus obtained was filtered to separate, washed, dried at 40° C. for a day, calcined at 280° C. for 1 hour under air stream and calcined successively at 600° C. for 2 hours under nitrogen stream to get a catalyst of the present invention having a composition of $Mo_{1.0}V_{0.3}Ti_{0.025}Sb_{0.1}K_{0.016}$.

(3) The Preparation of Comparative Catalyst A for US 2002/0115879 (Hinago et al.):

An aqueous raw material mixture was prepared by the same method as the above (1) except for that the raw materials was used in the amount of 34 times of the above (1) for spray-drying. The aqueous raw material mixture was subjected to a spray drying under conditions wherein the entrance and exit temperatures of a spray-drying apparatus were 230° C. and 120° C. to obtain a dried product. The dried product was calcined at 640° C. for 2 hours under nitrogen stream to obtain Comparative Catalyst A. Said drying conditions and calcining conditions are the same as Example 1 of Hinago et al.

(4) The Preparation of Comparative Catalyst B for WO 99/03825:

A dried product was prepared by the same method as above (3) because the drying conditions of the aqueous raw material mixture (slurry) were not shown in Reference Example 1 of WO 99/03825. The dried product was treated at 300° C. for 2 hours under an air stream and then calcined at 640° C. for 2 hours under a nitrogen stream to obtain the comparative catalyst B. The conditions of treating and calcining mentioned above are the same as that of Reference Example 1 of WO 99/03825.

(B) Comparison of Forms of Catalysts

Figure 1:
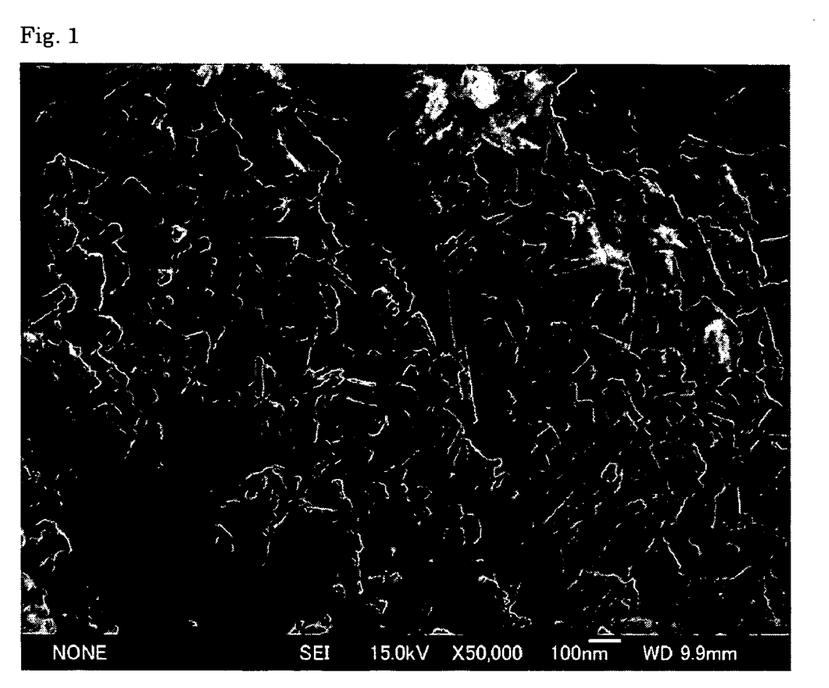
FIG. 1 is a photograph from an electron microscope of the catalyst of the present invention obtained in Example C.
Figure 2:
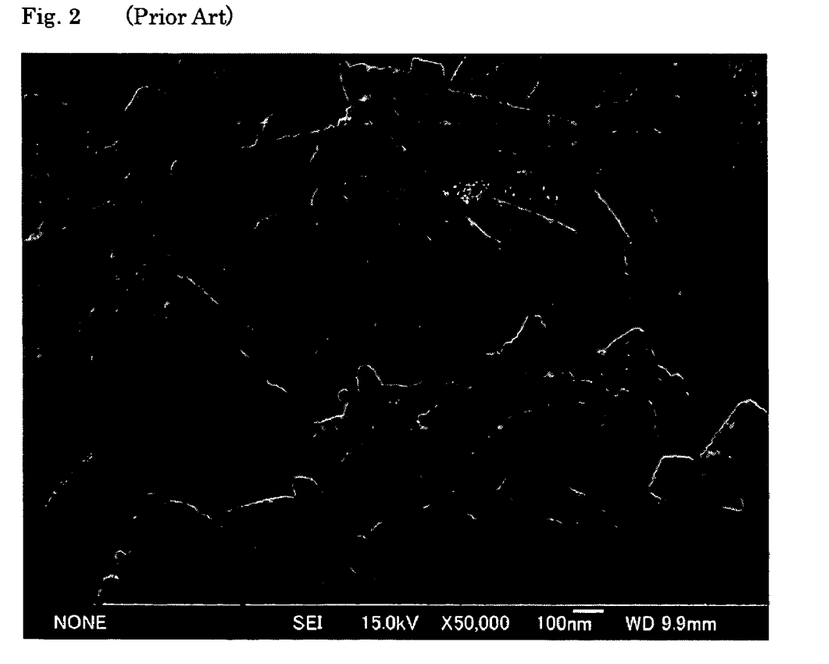
FIG. 2 is a photograph from an electron microscope of a prior art catalyst obtained in Example C.
Figure 3:
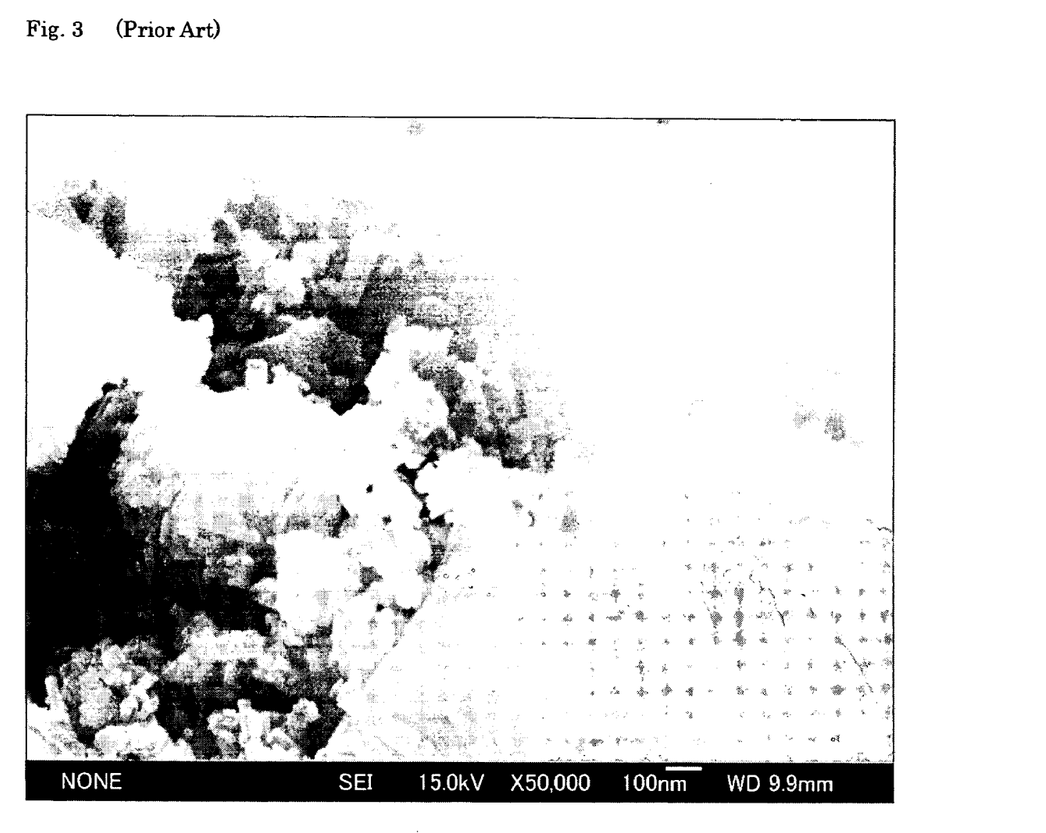
FIG. 3 is a photograph from an electron microscope of another prior art catalyst obtained in Example C.

Electron microscopes of the catalysts obtained by above (2), (3) and (4) are shown in FIG. 1 (Present Catalyst), FIG. 2 Comparative Catalyst A) and FIG. 3 (Comparative Catalyst B). FIG. 1 (Present Catalyst) shows needle crystals although FIG. 2 (Comparative Catalyst A) and FIG. 3 (Comparative Catalyst B) do not show such needle crystals.

(C) Comparison of Performance of Catalysts for Production of Acrylic Acid from Propane.

The vapor-phase catalytic oxidation of propane was carried out using Present Catalyst and Comparative Catalyst B respectively, the same as Example A1 except that the reaction temperature was changed to 360° C.

The results are shown in Table 1:

TABLE 1

| Catalyst | Conversion of Propane % | Acrylic acid of Selectivity % | Yields of Acrylic acid % |
|---|---|---|---|
| Present Catalyst | 47.4 | 33.9 | 16.0 |
| Comparative Catalyst B | 0.3 | 0.0 | 0.0 |

It can be understood from the above table that Comparative Catalyst (B) (non-needle crystal) has no ability to produce acrylic acid by the vapor-phase catalytic oxidation of propane.

INDUSTRIAL APPLICABILITY

A catalyst of the present invention has a high activity and is therefore very useful as a catalyst for producing an unsaturated oxygen-containing compound by the vapor-phase catalytic oxidation reaction of an alkane.

The invention claimed is:

1. A method for producing an unsaturated oxygen-containing compound by the vapor-phase catalytic oxidation of an alkane, comprising subjecting an alkane to vapor-phase catalytic oxidation in the presence of a catalyst, wherein at least 50% of said catalyst has an appearance of needle crystal by observation by an electron microscope and having a specific surface area of 2-50 m²/g, which catalyst is represented by general Formula (1) as shown below, $$Mo_{1.0}V_aTi_bX_cY_dO_e \qquad (1)$$

wherein, X represents at least one element selected from the group consisting of Sb and Te; Y represents at least one element selected from the group consisting of Nb, W and Zr; a, b, c, d and e represent atomic ratios of their respective elements, with $0<a<0.7$, $0<b<0.3$, $0<c<0.7$, $0.1\leq d<0.3$ and e is a number determined by the oxidation states of the other elements than oxygen.

2. The method according to claim 1, wherein said catalyst is represented by general Formula (2) as shown below, $$Mo_{1.0}V_aTi_bX_cY_dZ_fO_e \qquad (2)$$

wherein, X, Y, a, b, c, d and e have the same meanings as in formula (1), Z represents at least one element selected from the group consisting of Li, Na, K, Rb, Cs, Mg, Ca and Sr, and f represents an atomic ratio of Z, with $0<f<0.1$.

3. The method according to claim 1, wherein the alkane is propane and the unsaturated oxygen-containing compound is at least one selected from the group consisting of acrolein and acrylic acid.

4. The method according to claim 1, wherein the catalyst specific surface area is 2-20 m²/g.

5. The method of claim 1, wherein said catalyst is prepared by hydrothermal synthesis.

6. The method of claim 5, wherein said hydrothermal synthesis is carried out at a reaction temperature of greater than 100° C.

* * * * *

UNITED STATES PATENT AND TRADEMARK OFFICE
CERTIFICATE OF CORRECTION

| | | |
|---|---|---|
| PATENT NO. | : 7,642,214 B2 | Page 1 of 1 |
| APPLICATION NO. | : 11/494846 | |
| DATED | : January 5, 2010 | |
| INVENTOR(S) | : Kobayashi et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 412 days.

Signed and Sealed this

Sixteenth Day of November, 2010

David J. Kappos
*Director of the United States Patent and Trademark Office*